(12) United States Patent
Childers et al.

(10) Patent No.: US 10,143,837 B2
(45) Date of Patent: Dec. 4, 2018

(54) METHOD FOR MANUFACTURING AN IMPLANTABLE CARDIAC ELECTROTHERAPY LEAD

(71) Applicant: PACESETTER, INC., Sylmar, CA (US)

(72) Inventors: Michael Childers, Tujunga, CA (US); Keith Victorine, Valencia, CA (US); Steven R. Conger, Agua Dulce, CA (US); Alexander Farr, Woodland Hills, CA (US)

(73) Assignee: PACESETTER, INC., Sylmar, CA (US)

( * ) Notice: Subject to any disclaimer, the term of this patent is extended or adjusted under 35 U.S.C. 154(b) by 0 days.

(21) Appl. No.: 15/951,038

(22) Filed: Apr. 11, 2018

(65) Prior Publication Data

US 2018/0229026 A1    Aug. 16, 2018

Related U.S. Application Data

(62) Division of application No. 14/691,063, filed on Apr. 20, 2015, now Pat. No. 9,968,776.

(51) Int. Cl.
   *A61N 1/05* (2006.01)

(52) U.S. Cl.
   CPC ............ *A61N 1/056* (2013.01); *A61N 1/0563* (2013.01)

(58) Field of Classification Search
   CPC .......... A61N 1/04; A61N 1/0471; A61N 1/05; A61N 1/0551; A61N 1/0553; A61N 1/056; A61N 1/0563; B29C 41/20

USPC ...................... 607/2, 116; 600/373
   See application file for complete search history.

(56) References Cited

U.S. PATENT DOCUMENTS

| | | | | |
|---|---|---|---|---|
| 5,851,226 | A * | 12/1998 | Skubitz .................. | A61N 1/056 607/126 |
| 5,908,447 | A * | 6/1999 | Schroeppel .......... | A61N 1/3704 607/126 |
| 6,123,699 | A * | 9/2000 | Webster, Jr. ........... | A61B 5/015 604/528 |
| 6,249,708 | B1 * | 6/2001 | Nelson ................... | A61N 1/056 607/122 |
| 8,386,055 | B2 * | 2/2013 | Cole ........................ | A61N 1/05 600/372 |
| 8,886,336 | B2 * | 11/2014 | Lim ........................ | A61N 1/05 607/116 |
| 9,968,776 | B2 * | 5/2018 | Childers ............... | A61N 1/0563 |
| 2002/0099430 | A1 * | 7/2002 | Verness .................. | A61N 1/056 607/122 |
| 2003/0236562 | A1 * | 12/2003 | Kuzma ................ | A61N 1/0529 607/122 |
| 2004/0015221 | A1 * | 1/2004 | Kuzma ................ | A61N 1/0529 607/116 |
| 2004/0024440 | A1 * | 2/2004 | Cole ........................ | A61N 1/05 607/122 |

(Continued)

*Primary Examiner* — Christopher A Flory

(57) ABSTRACT

Methods of manufacturing implantable electrotherapy leads are disclosed herein. In one embodiment, the lead is manufactured by receiving a length of lead stock, forming an opening in a jacket at an intermediate location, interrupting a selected cable conductor, connecting a crimp connector to a proximal portion of the interrupted conductor at the opening, connecting a conductive element to the crimp connector, and removing at least a segment of a distal portion of the interrupted conductor from a lead body.

12 Claims, 9 Drawing Sheets

(56) References Cited

U.S. PATENT DOCUMENTS

| | | | | |
|---|---|---|---|---|
| 2006/0142703 A1* | 6/2006 | Carter | A61M 25/0015 | 604/264 |
| 2007/0168004 A1* | 7/2007 | Walter | A61N 1/0551 | 607/116 |
| 2007/0168007 A1* | 7/2007 | Kuzma | A61N 1/0551 | 607/116 |
| 2009/0326626 A1* | 12/2009 | Swoyer | A61N 1/0551 | 607/116 |
| 2010/0121421 A1* | 5/2010 | Duncan | A61N 1/05 | 607/116 |
| 2010/0204767 A1* | 8/2010 | Zhao | A61N 1/05 | 607/122 |
| 2011/0202118 A1* | 8/2011 | Cole | A61N 1/05 | 607/116 |
| 2011/0218603 A1* | 9/2011 | Victorine | A61N 1/05 | 607/116 |
| 2012/0065699 A1* | 3/2012 | Bedenbaugh | A61B 5/0478 | 607/45 |
| 2013/0247374 A1* | 9/2013 | Li | A61N 1/056 | 29/860 |
| 2014/0067030 A1* | 3/2014 | Walker | A61N 1/056 | 607/116 |
| 2014/0067033 A1* | 3/2014 | Victorine | A61N 1/05 | 607/116 |
| 2014/0081364 A1* | 3/2014 | Victorine | A61N 1/05 | 607/116 |
| 2014/0088672 A1* | 3/2014 | Bedenbaugh | A61B 5/0478 | 607/116 |
| 2014/0180371 A1* | 6/2014 | Leven | A61N 1/0551 | 607/116 |
| 2015/0080995 A1* | 3/2015 | Seeley | A61N 1/05 | 607/116 |
| 2015/0209579 A1* | 7/2015 | Olsen | A61N 1/3718 | 607/116 |
| 2015/0250999 A1* | 9/2015 | DiGiore | A61N 1/05 | 29/860 |
| 2016/0303366 A1* | 10/2016 | Childers | A61N 1/0563 | |

* cited by examiner

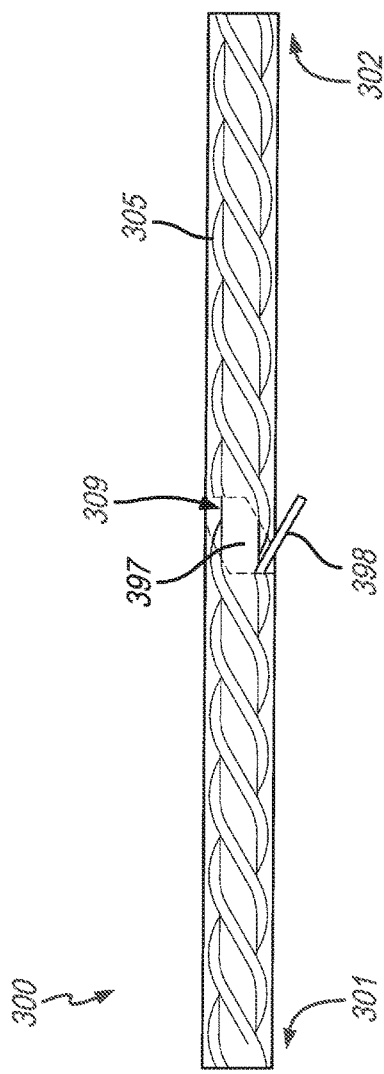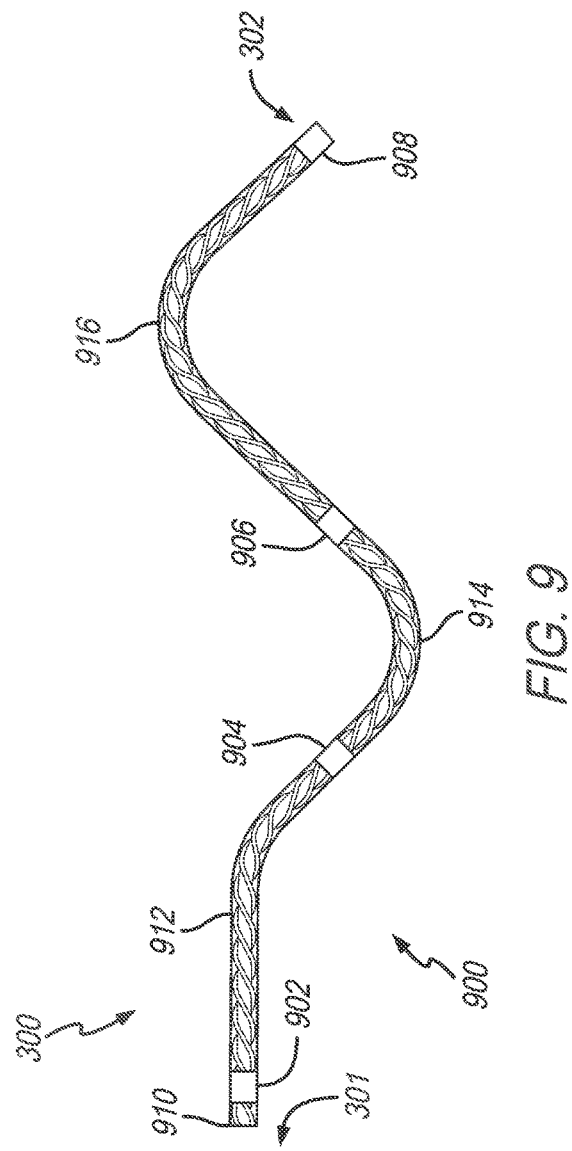

METHOD FOR MANUFACTURING AN IMPLANTABLE CARDIAC ELECTROTHERAPY LEAD

CROSS REFERENCE TO RELATED APPLICATIONS

This is a division of U.S. patent application Ser. No. 14/691,063, filed Apr. 20, 2015.

FIELD OF THE INVENTION

The present invention relates to medical apparatus and methods of manufacturing such apparatus. More specifically, the present invention relates to implantable cardiac electrotherapy leads and methods of manufacturing such leads.

BACKGROUND OF THE INVENTION

Current implantable cardiac electrotherapy leads (e.g., cardiac resynchronization therapy (CRT) leads, bradycardia therapy leads, and tachycardia therapy leads) typically include multiple cable conductors. Each of the cable conductors may be electrically connected to an electrode, shock coil, or other conductive element at some location along the lead to allow an electrical circuit to be formed in conjunction with the cardiac electrical system of a patient by way of a lead coupled to a pacemaker, defibrillator, or other cardiac therapy device.

While ongoing development of implantable cardiac electrotherapy leads has resulted in at least some newer leads which have a helically wound lead body providing improved reliability, especially with respect to reduced cable fatigue, fractures, and abrasion, other potential concerns remain, such as electrical isolation between the cable conductors and overall stiffness of the lead. More specifically, lack of electrical isolation between cable conductors may render the cardiac therapy device inoperative. In at least some cases, the possibility of unintended electrical coupling between cable conductors may be particularly pronounced at a distal end of the lead opposite the cardiac therapy device.

Further, excessive stiffness of the lead may result in reduced flexibility for those applications in which the lead may benefit from flexibility so that the attached conductive elements may reach all intended destinations in the body. Oppositely, some applications may require more strength and, consequently, less flexibility so that, for example, the lead or a conductive element attached thereto may be torqued or pushed to properly position the lead.

With the above aspects in mind, as well as others not explicitly discussed herein, various embodiments of an implantable cardiac electrotherapy lead, as well as embodiments for manufacturing such leads, are disclosed herein.

SUMMARY

In one embodiment, an implantable cardiac electrotherapy lead may include a plurality of cable conductors within at least one lumen of an insulating jacket. A first one and a second one of the cable conductors may include a proximal end at a proximal end of the jacket, the second one of the cable conductors may extend to at least the distal end of the jacket, and the first one of the cable conductors may include a distal end at an intermediate location between the proximal end and the distal end of the jacket. The lead may also include a crimp connector connected to the first one of the cable conductors at the intermediate location, as well as a conductive element that is connected to the crimp connector. A number of cable conductors along the proximal portion of the jacket are greater than a number of cable conductors along at least a segment of the distal portion of the jacket.

In another embodiment, a method of manufacturing an implantable cardiac electrotherapy lead may include receiving a length of lead stock, in which the stock comprises a plurality of cable conductors and an insulating jacket defining at least one lumen within which the cable conductors are located. An opening may be formed in the jacket at an intermediate location between a proximal end and a distal end of the length of lead stock. At least one of the cable conductors may be interrupted at the opening in the jacket to form a proximal portion and a distal portion of the at least one cable conductor. A crimp connector may be connected to the proximal portion at the opening, and a conductive element may be connected to the crimp connector. At least a segment of the distal portion of the at least one cable conductor may be removed.

While multiple embodiments are disclosed, still other embodiments of the present invention will become apparent to those skilled in the art from the following detailed description, which depicts and describes illustrative embodiments of the invention. As will be realized, the invention is capable of modifications in various aspects, all without departing from the scope of the present invention. Accordingly, the drawings and detailed description are to be regarded as illustrative in nature and not restrictive.

BRIEF DESCRIPTION OF THE DRAWINGS

FIG. 8 is a partial longitudinal side view of the example lead body of FIG. 5 with a second opening in the outer jacket and core jacket to access and remove a segment of a distal portion of the interrupted cable conductor.

FIG. 9 is partial longitudinal side view of an example lead of the lead body of FIG. 8, to which several conductive elements have been connected to the proximal portion of multiple interrupted cable conductors.

DETAILED DESCRIPTION

The following detailed description relates to implantable cardiac electrotherapy leads. In one example, a lead may include a plurality of cable conductors within at least one lumen of an insulating jacket. A first one and a second one of the cable conductors may include a proximal end at a proximal end of the jacket, the second one of the cable conductors may extend to at least a distal end of the jacket, and the first one of the cable conductors may include a distal end at an intermediate location between the proximal end and the distal end of the jacket. The lead may also include a crimp connector connected to the first one of the cable conductors at the intermediate location, as well as a conductive element that is connected to the crimp connector. A number of cable conductors along the proximal portion of the jacket may be greater than a number of cable conductors along at least a segment of the distal portion of the jacket.

In some embodiments, as disclosed below, a method of manufacturing an implantable cardiac electrotherapy lead may include receiving a length of lead stock that includes a plurality of cable conductors and an insulating jacket defining at least one lumen in which the cable conductors are located. An opening in the jacket may be formed at an intermediate location between a proximal end and a distal end of the length of lead stock. At least one of the cable conductors may be interrupted at the opening to form a proximal portion and a distal portion of the at least one cable conductor. A crimp connector may be connected to the proximal portion of the at least one cable conductor at the opening, and a conductive element may be connected to the crimp connector. At least a segment of the distal portion of the at least one cable conductor may be removed from the at least one lumen.

As a result of at least some of the embodiments discussed in greater detail below, the interruption of the at least one cable conductor may facilitate greater electrical isolation between the at least one cable conductor and other cable conductors of the lead. This isolation may be further enhanced by interrupting the distal portion of the at least one cable conductor at a second opening, or by removing the entirety of the at least one cable conductor from the lead. Other aspects and potential advantages of the embodiments disclosed herein are also presented below.

Figure 1A:
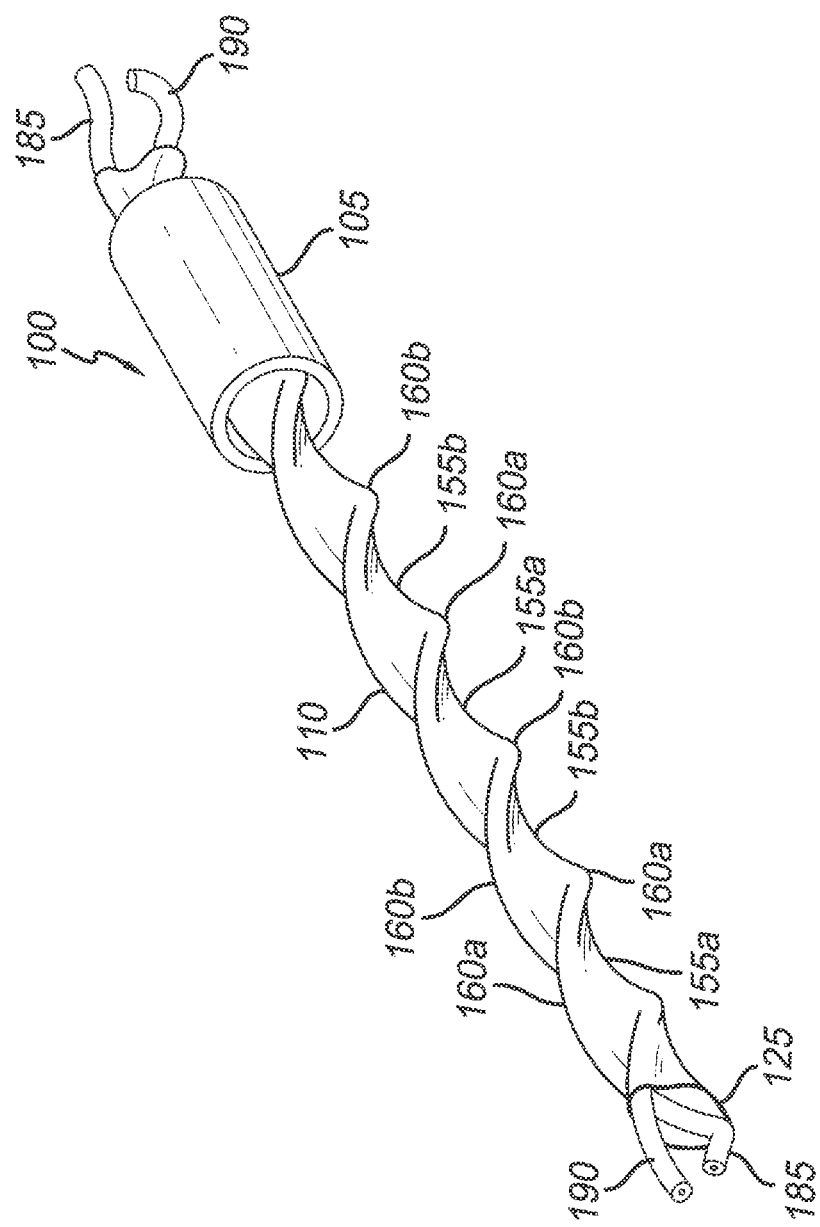
FIG. 1A is an isometric view of a longitudinal segment of an example helically wound lead body including two cable conductors, in which an outer jacket of the lead body is largely hidden to reveal a helical core assembly of the lead body.
Figure 1B:
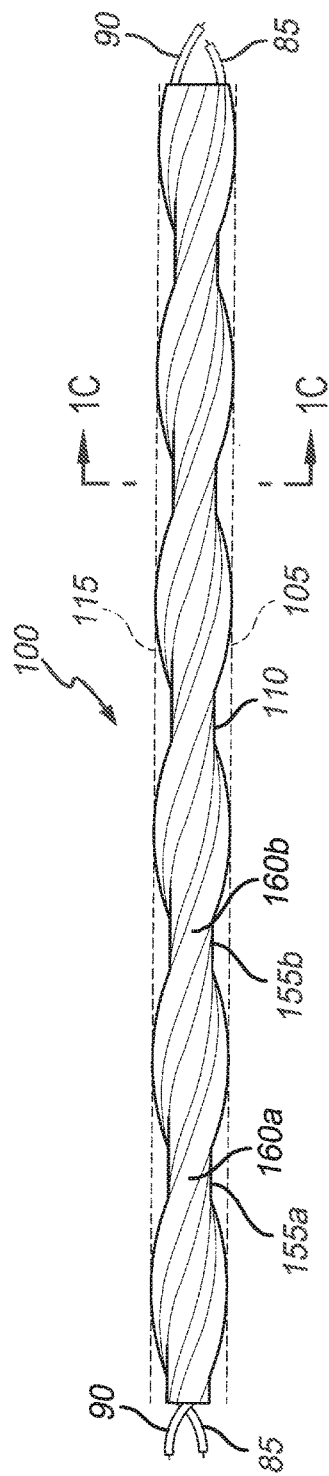
FIG. 1B is a longitudinal side view of the example lead body of FIG. 1A in which the outer jacket is depicted in phantom lines to reveal the helical core assembly.
Figure 1C:
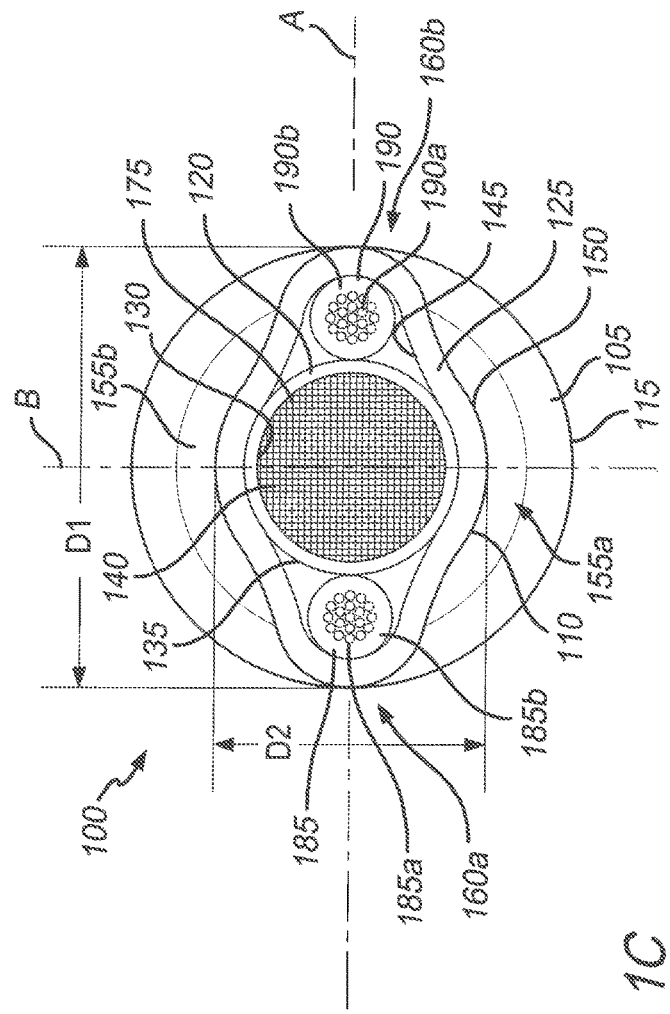
FIG. 1C is a transverse cross-sectional view of the example lead body of FIG. 1A as taken along section line 1C-1C in FIG. 1B.

For a discussion regarding a lead body upon which embodiments disclosed herein may be based, reference is made to FIGS. 1A-1C. FIG. 1A is an isometric view of a longitudinal segment of an example lead body 100 including two cable conductors 185 and 190, in which an outer jacket 105 of the lead body 100 is largely hidden to reveal a helical core assembly 110 of the lead body 100. FIG. 1B is a longitudinal side view of the lead body 100 of FIG. 5A in which the outer jacket 105 is depicted in phantom lines to reveal the helical core assembly 110. FIG. 1C is a transverse cross-sectional view of the lead body 100 as taken along section line 1C-1C in FIG. 1B.

As indicated in FIGS. 1A-1C, in one embodiment, the helical core assembly 110 forms a central or core portion 110 of the lead body 100 and is enclosed by the outer jacket 105, which forms an outer circumferential surface 115 of the lead body 100. The outer jacket 105 may be formed of silicone rubber, silicone rubber—polyurethane—copolymer (SPC), polyurethane, or another material. As mentioned below, other types of lead bodies employable in the embodiments described herein may not employ an outer jacket 105.

As illustrated in FIG. 1C, in one embodiment, the helical core assembly 110 includes an inner liner 120, a pair of cable conductors 185, 190, and a core jacket 125. The inner liner 120 includes inner and outer circumferential surfaces 130, 135. The inner circumferential surface 130 of the inner liner 120 may define a central lumen 140 of the lead body 100 through which a guidewire and/or stylet may be extended during the revision and implantation of the resulting lead. In one embodiment, the inner liner 120 may be formed of a polymer material such as ethylene tetrafluoroethylene (ETFE), polytetrafluoroethylene ("PTFE"), and/or another material.

As further indicated in FIG. 1C, in one embodiment, the two conductors 85, 90 are located outside the inner liner 120 adjacent to the outer circumferential surface 135 of the inner liner 120. The two conductors 85, 90 may be evenly radially spaced from each other about the outer circumferential surface 135 of the inner liner 120. The conductors 85, 90 may have electrically conductive cores 185a, 190a, and each of the cable conductors 185, 190 may or may not have corresponding individual electrical insulation jackets 185b, 190b. In examples in which the cable conductors 185, 190 have insulation jackets 185b, 190b, the insulation jackets 185b, 190b may be formed of a polymer material such as ETFE, PTFE, and/or another material. The electrically conductive cores 185a, 190a may be multi-wire or multi-filar cores or solid single wire cores.

As depicted in FIG. 1C, the helical core assembly 110 may have two cable conductors 185, 190 that are evenly radially spaced apart from each other about the inner liner 120. However, in other embodiments, the cable conductors 185, 190 may have other arrangements. For example, the helical core assembly 110 may include greater than two cable conductors 185, 190, and the cable conductors 185, 190 may be routed in groups (e.g., pairs) of conductors such that the conductors are not radially spaced apart. More specifically, the coils of the helically routed conductors 185, 190 may actually contact each other despite having a pitch that results in an overall length that is not substantially greater than a straight-routed conductor.

As can be understood from FIGS. 1A and 1B, the cable conductors 185, 190 longitudinally extend along the outer circumferential surface 135 of the inner liner 120 in a helical wind about a central axis of the lead body 100, such as that defined by the inner liner 120. In other examples, however, the conductors 185, 190 may extend directly along the length of the lead body 100 without any wind, helical or otherwise. In some embodiments, the pitch of the helically-routed cable conductors 185, 190 is between approximately 0.05 inches and approximately 0.3 inches.

As shown in FIG. 1C, the core jacket 125 includes an inner surface 145 and an outer surface 150. The core jacket 125 extends about the cable conductors 185, 190 and the inner liner 120, thereby enclosing the inner liner 120 and the conductors 185, 190 within the core jacket 125. In other embodiments, a core jacket 125 may not be utilized.

As further illustrated in FIG. 1C, the core jacket 125 may fit snuggly about the inner liner 120 and the cable conductors 185, 190 such that the inner surface 145 of the core jacket 125 extends along and generally conforms to portions of the outer circumferential surface 135 of the inner liner 120 and the outer surfaces of the cable conductors 185, 190 (e.g., the outer surfaces of the conductor insulation 185b, 190b, where present). In examples in which two cable conductors 185, 190 are employed, the resulting transverse cross-section of the helical core assembly 110 may have a first diameter D1, which is aligned with a first axis A extending through the center points of the cable conductors 185, 190 and the central lumen 140, that is substantially larger than a second diameter D2, which is aligned with a second axis B that is generally perpendicular to the first axis A. In one example, the first diameter D1 may be approximately 0.05 inches.

As shown in FIGS. 1A and 1B, as a result of the helical routing of the cable conductors 185, 190 about the inner liner 120 and the general conforming of the core jacket 125, the outer surface 150 of the core jacket 125 may also be helical, thus defining two helically extending troughs 155a, 155b separated by two helically extending ridges 160a, 160b. Where the helical core assembly 110 includes three, four, or more helically-routed conductors, and the core jacket 125 generally conforms to the cable conductors 185, 190 and the inner liner 120, the outer surface 150 of the core jacket 125 may exhibit a corresponding number of troughs and ridges.

As can be understood from FIGS. 1A-1C, the location and routing of each helically extending ridge 160a, 160b corresponds to and generally matches the location and routing of a specific helically-routed cable conductor 185, 190. The location and routing of each helically extending trough 155a, 155b corresponds and generally matches the location of a space centered between a pair of helically-routed cable conductors 185, 190.

As indicated in FIG. 1C, in one embodiment, the helical core assembly 110 is encased or imbedded in the material of the outer jacket 105 of the lead body 100, the outer circumferential surface 115 of the outer jacket 105 forming the outer circumferential surface 115 of the lead body 100. As indicated in FIG. 1C, the outer jacket 105 may in-fill voids between the lead body outer circumferential surface 115 and the core jacket outer surface 150 in the vicinity of the troughs 155a, 155b. The result may be a lead body 100 with an outer circumferential surface 115 having a generally circular shape in transverse cross-section and generally uniform diameter along its length, despite the helical core assembly 110 having a transverse cross-section that is semi-elliptical.

As mentioned above, the lead body 100 may include any number of cable conductors, including two conductors, three conductors, and so on. For example, FIG. 2, which is a transverse cross-sectional view similar to FIG. 1A, depicts a lead body 200 in which four cable conductors 185, 186, 190, and 191 are helically wound about an inner liner 120 that defines a central lumen 140. Also similar to the lead body 100, a core jacket 125 may surround the four cable conductors 185, 186, 190, and 191 and the inner liner 120. In addition, an outer jacket 105 may be employed to cover substantially the core jacket 125, potentially to render a substantially circular cross-section for the lead body 200. In other examples, an outer jacket 105 may not be utilized. As with the diameter D1 of the lead body 100 of FIG. 1C, the largest diameter of the lead body 200 may be approximately 0.05 inches.

Figure 3:
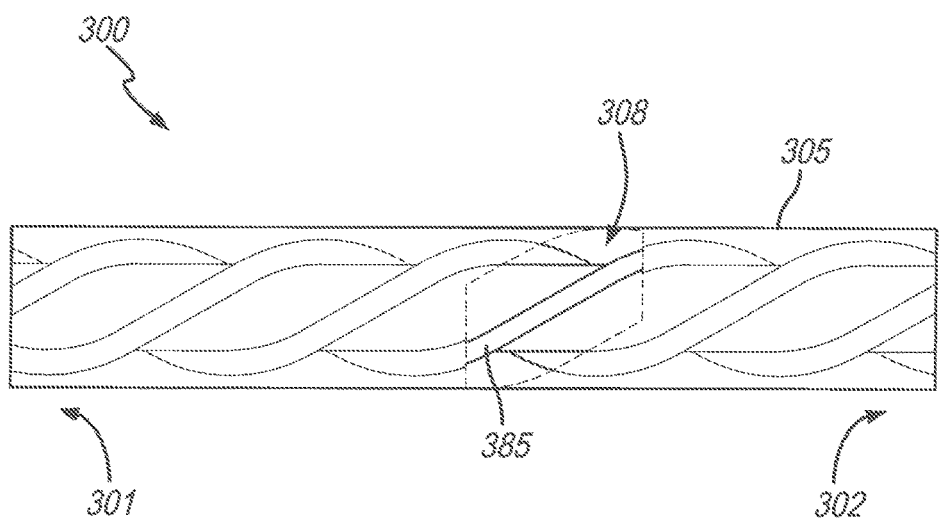
FIG. 3 is a partial longitudinal side view of an example lead body with an opening in an outer jacket and a core jacket to access a cable conductor within.

Any of the example lead bodies 100, 200 described above, as well as others, may be employed to produce implantable cardiac electrotherapy leads for monitoring, synchronization, and other cardiac electrotherapy uses. FIG. 3 is a partial longitudinal side view of an example lead body 300 that is in the process of being modified to produce such a lead. In one embodiment, the lead body 300 may be a length of pre-manufactured lead stock that has been cut from a spool or other container of lead stock. More specifically, the lead body 300 may include multiple cable conductors, including a cable conductor 385 that has been selected for a connection with a conductive element at a particular intermediate location between a proximal end 301 and a distal end 302 of the lead body 300. In one example, the proximal end 301 is to be prepared for coupling with a pacemaker, defibrillator, or other cardiac therapy device, with one or more conductive elements to be located along the lead body 300 from the proximal end 301 to the distal end 302 and connected to selected cable conductors of the lead body 300.

Figure 2:
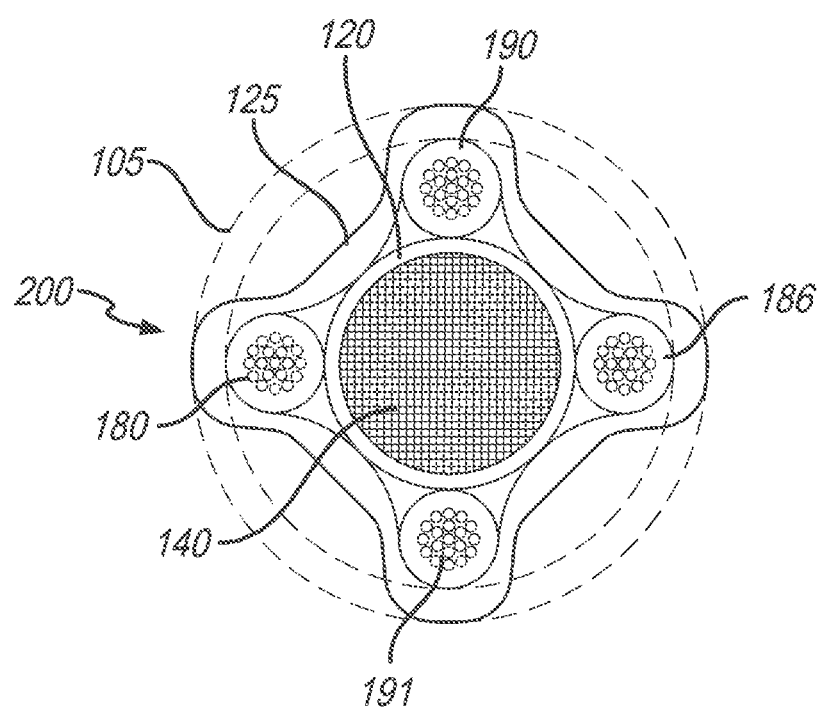
FIG. 2 is a transverse cross-sectional view of an example lead body including four cable conductors.

As shown, the lead body 300 may include four helically wound cable conductors, including the selected cable conductor 385, similar to the lead body 200 of FIG. 2, although other numbers and types of lead bodies may be employed in other examples. As shown, one or more of the cable conductors, including the selected cable conductor 385, may be coated with an individual insulating sleeve or material, as mentioned above.

Figure 4:
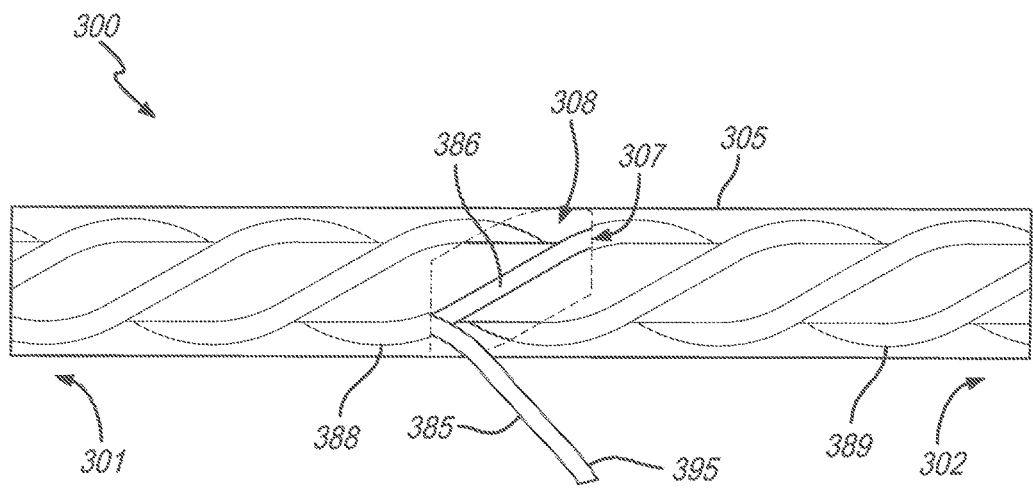
FIG. 4 is a partial longitudinal side view of the example lead body of FIG. 3 in which the cable conductor being accessed is interrupted.

In this example, a technician or other personnel, or a machine configured to perform the various operations described herein automatically, has formed an opening 308 in an outer jacket 305 and a core jacket (not explicitly shown in FIG. 3), such as by way of cutting or other means to gain mechanical access to the selected cable conductor 385 at a desired location for connection to the conductive element. In other embodiments, the outer jacket 305 or the core jacket may not be present in the lead body 300. In other examples, the outer jacket 305 and/or the core jacket may not extend long an entirety of the lead body 300, FIG. 4 is a partial longitudinal side view of the example lead body 300 of FIG. 3 in which the selected cable conductor 385 accessed is interrupted. In one example, a technician may cut the selected cable conductor 385 with cutters, pliers, or another tool to form a proximal portion 388 and a distal portion 389 of the selected cable conductor 385. In one particular example, the technician may cut or interrupt the selected cable conductor 385 at a distal end 387 of the opening 308 to allow the portion of the selected cable conductor 385 that is exposed via the opening 308 to remain accessible for attaching a crimp connector thereto. As shown in FIG. 4, the accessible portion of the selected cable conductor 385 may be temporarily extracted from the outer jacket 305 and/or core jacket to facilitate access to an exposed distal end 395 of the proximal portion 388 of the selected cable conductor 385 to allow the placement of a crimp connector over the end 395.

In this example, by cutting or otherwise interrupting the selected cable conductor 385, as opposed to exposing the selected cable conductor 385 for subsequent connection to a conductive element, such as an electrode or shock coil, the proximal portion 388 and the distal portion 389 of the selected cable conductor 385 may be effectively isolated electrically. Such isolation may help prevent short circuits or other unwanted electrical coupling between the proximal portion 388 of the selected cable conductor 385 and other cable conductors of the lead body 300, such as what may occur as a result of a connector being attached at the distal end 302 of the lead body 300, at which the various cable conductors terminate.

Figure 5:
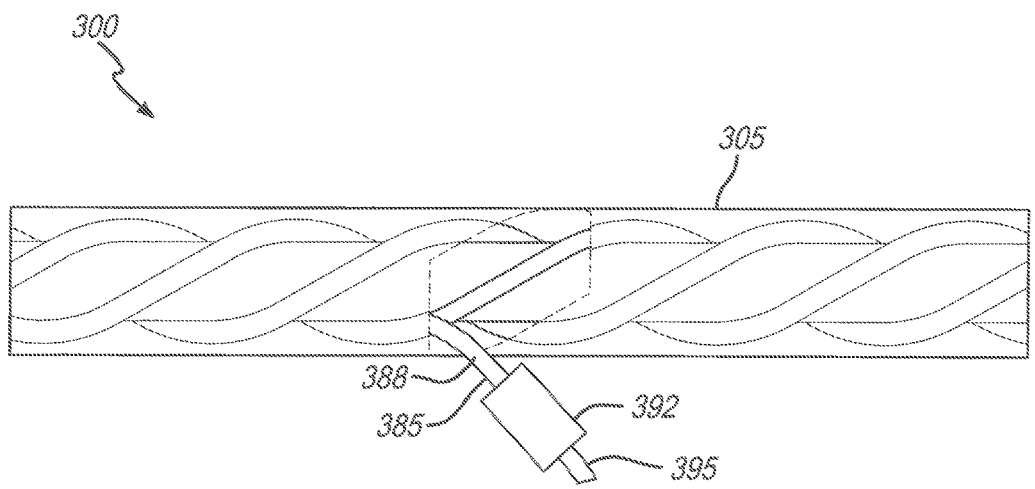
FIG. 5 is a partial longitudinal side view of the example lead body of FIG. 4 with a crimp connector attached to a proximal portion of the interrupted cable conductor being accessed.
Figure 6A:
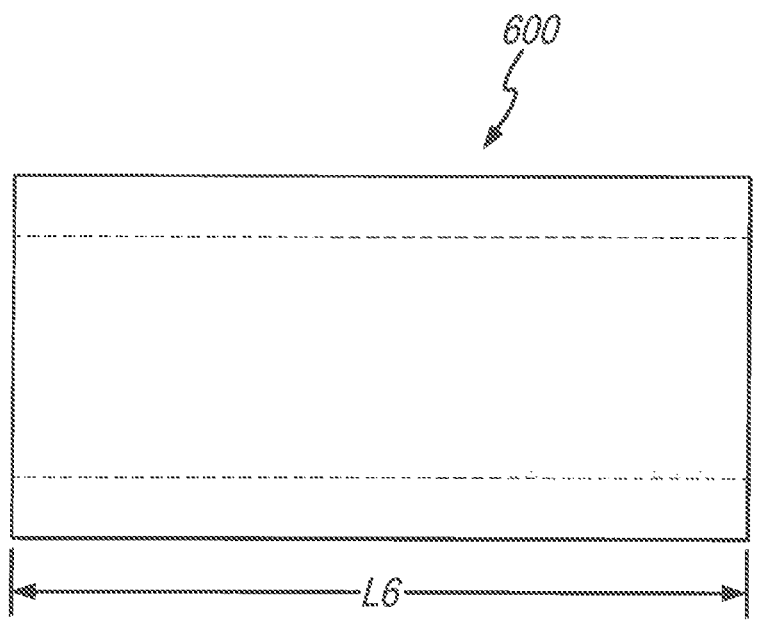
FIG. 6A is an enlarged side view of an example cylindrical crimp connector for connecting a conductive element to the proximal portion of the interrupted cable conductor depicted in FIG. 5.
Figure 6B:
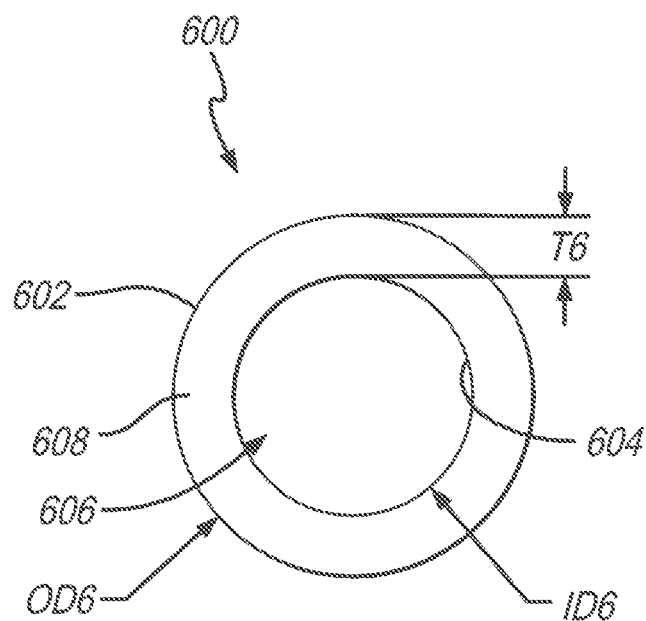
FIG. 6B is an enlarged end view of the example cylindrical crimp connector of FIG. 6A.

FIG. 5 is a partial longitudinal side view of the example lead body 300 of FIG. 4 with a crimp connector 392 attached to the proximal portion 388 of the interrupted cable conductor 385. In one example, the crimp connector 392 is slid over the distal end 395 of the proximal portion 388 of the selected cable conductor 385 such that the crimp connector 392 radially surrounds the selected cable conductor 385. One particular example crimp connector is illustrated in FIGS. 6A and 6B, while another example crimp connector is depicted in FIGS. 7A-7D, although many other types of crimp connectors may be mechanically and electrically coupled to the selected cable conductor 385 in other embodiments. In yet further examples, connectors other than crimp connectors may be employed.

FIG. 6A is an enlarged side view of an example cylindrical crimp connector 600 for connecting a conductive element to the proximal portion 388 of the interrupted cable conductor 385 depicted in FIG. 5, and FIG. 6B is an enlarged end view of the example cylindrical crimp connector 600 of FIG. 6A. Generally, the cylindrical crimp connector 600 may be fabricated from a strong, deformable, and electrically conductive material as a cylinder with an exterior radial surface 602 and defining a longitudinal channel 606 via an interior radial surface 604 extending along a central longitudinal axis of the cylinder. Consequently, the cylindrical crimp connector 600 includes two end faces 608 at opposing ends of the connector 600.

In one embodiment, the cylindrical crimp connector 600 may be a segment of pre-drawn tubing. In one embodiment, the cylindrical crimp connector 600 may be formed of a metal or alloy material (e.g., platinum-iridium, MP35N®, or stainless steel). In other embodiments, the cylindrical crimp connector 600 may be formed via other manufacturing processes, such as metal injection molding.

In a particular example, the cylindrical crimp connector 600 may have a length L6 of approximately 0.05 inches, an inner diameter ID6 of approximately 0.0165 inches, an outer diameter OD6 of approximately 0.025 inches, and a thickness T6 of approximately 0.004 inches. However, many different sizes and dimensions for the cylindrical crimp connector 600 may be utilized in other embodiments.

In examples in which the selected cable conductor 385 is covered with a layer or coating of insulation, the insulation may be stripped or otherwise removed from the selected cable conductor 385 prior to sliding the cylindrical crimp connector 600 over the distal end 395 of the proximal portion 388 of the selected cable conductor 385. The cylindrical crimp connector 600 may then be crimped using a crimping anvil and die, or other crimping tool or machine, to create a secure connection between the proximal portion 388 of the selected cable conductor 385 and the cylindrical crimp connector 600. Such crimping may, for example, deform the cylindrical crimp connector 600 to securely capture the proximal portion 388 of the selected cable conductor 385, thus altering the shape of the channel 606 of the cylindrical crimp connector 600 from a circular shape to a somewhat oval or other noncircular appearance. Accordingly, the selected cable conductor 385 may securely contact at least portions of the interior radial surface 604 to create an electrical connection therebetween.

Figure 7A:
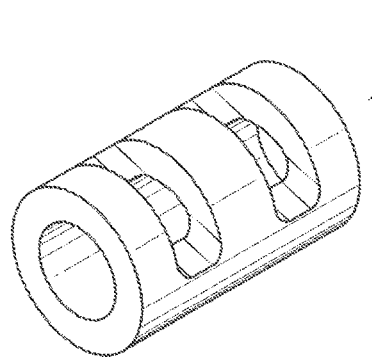
FIG. 7A is an enlarged oblique view of an example crimp-through crimp connector for connecting a conductive element to the proximal portion of the interrupted cable conductor depicted in FIG. 5.
Figure 7B:
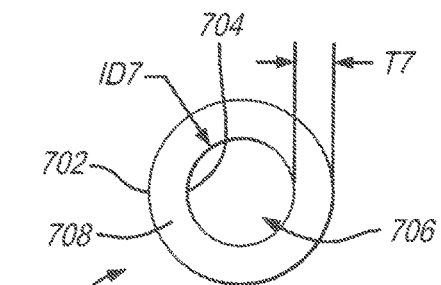
FIG. 7B is an enlarged end view of the example crimp-through crimp connector of FIG. 7A.
Figure 7C:
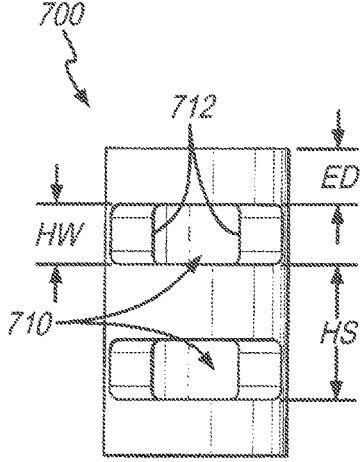
FIG. 7C is an enlarged top view of the example crimp-through crimp connector of FIG. 7A.
Figure 7D:
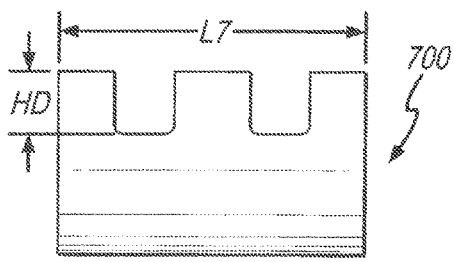
FIG. 7D is an enlarged side view of the example crimp-through crimp connector of FIG. 7A.

FIGS. 7A-7D depict various views of another type of crimp connector 392: a crimp-through crimp connector 700. More specifically, FIG. 7A is an enlarged oblique view of an example crimp-through crimp connector 700 for connecting a conductive element to the proximal portion 388 of the interrupted cable conductor 385 depicted in FIG. 5, FIG. 7B is an enlarged end view of the example crimp-through crimp connector 700 of FIG. 7A, FIG. 7C is an enlarged top view of the example crimp-through crimp connector 700 of FIG. 7A, and FIG. 7D is an enlarged side view of the example crimp-through crimp connector 700 of FIG. 7A. Similar to the cylindrical crimp connector 600, the crimp-through crimp connector 700 may be fabricated from a strong, deformable, and electrically conductive material taking the general shape of a cylinder with an exterior radial surface 702 and defining a longitudinal channel 706 via an interior radial surface 704 extending along a central longitudinal axis of the cylinder. Accordingly, the crimp-through crimp connector 700 includes two end faces 708 at opposing ends of the connector 700.

As with the cylindrical crimp connector 600, the crimp-through crimp connector 700, in one embodiment, may be a segment of pre-drawn tubing. In one embodiment, the crimp-through crimp connector 700 may be formed of a metal or alloy material (e.g., platinum-iridium, MP35N®, or stainless steel). In other embodiments, the crimp-through crimp connector 700 may be formed via other manufacturing processes, such as metal injection molding, and so on.

In a particular example, the crimp-through crimp connector 700 may have a length L7 of approximately 0.04 inches, an inner diameter ID7 ranging approximately from 0.012 inches to 0.014 inches, and a wall thickness T7 ranging approximately from 0.004 inches to 0.005 inches. However, many different sizes and dimensions for the crimp-through crimp connector 700 other than those disclosed herein may be utilized in other embodiments.

Unlike the cylindrical crimp connector of FIGS. 6A and 6B, the crimp-through crimp connector 700, when crimped onto the distal end 395 of the proximal portion 388 of the selected cable conductor 385, may be configured to penetrate insulation that may be covering the selected cable conductor 385, thus potentially eliminating a need to remove the insulation from the area of interest of the selected cable conductor 385 prior to placing and crimping the crimp-through crimp connector 700 onto the selected cable conductor 385.

To provide such a feature, the crimp-through crimp connector 700 may define one or more splice openings 710 joining the interior radial surface 704 and the exterior radial surface 702, and having one or more relatively sharp edges 712 at the interior radial surface 704. In one embodiment, each splice opening 710 may be formed by laser cutting, resulting in the sharp edges 712 where the interior radial surface 704 intersects the splice opening 710.

The splice openings 710 may be any shape. As shown in FIGS. 7A and 7C, the splice openings 30 may be in the shape of a rectangular slot and may be oriented transverse to the longitudinal axis of the crimp-through crimp connector 700. In the case of a slot-type splice opening 710, the slot may extend across the crimp-through crimp connector 700 and have a length substantially equal to the inner diameter ID7 42 associated with the channel 706.

When the crimp-through crimp connector 700 is squeezed, pressed, or otherwise caused to crimp the proximal portion 388 of the selected cable conductor 385, the sharp edges 712 formed between each splice opening 712 and the interior radial surface 704 may cause the insulation of the selected cable conductor to be severed to promote electrical contact between the crimp-through crimp connector 700 and the conductive core of the proximal portion 388 of the selected cable conductor 785. In the example of FIGS. 7A-7D, this severing of the insulation may occur at both of the two splice openings 710 depicted therein. Moreover, this crimping process may cause the proximal portion 388 of the selected cable conductor 385 to be secured within the connector 700 due to frictional resistance between the cable conductor 385 and the interior radial surface 704, as well as to bearing-type resistance between bulging portions of the cable conductor 385 extending through the splice openings 710 toward the exterior radial surface 702.

In other embodiments, the splice openings 710 may not extend all the way to the external radial surface 702 of the connector 700. In this embodiment, the splice opening 710 may comprise a recess on the internal radial surface 704, allowing for similar severing and connection capabilities as those described above. Other variations of the crimp-through crimp connector 700 are possible in other examples as well.

FIG. 8 is a partial longitudinal side view of the example lead body 300 of FIG. 5 with a second opening 309 in the outer jacket 305 and core jacket (not explicitly shown in FIG. 8) to access and remove a segment 398 of the distal portion 302 of the interrupted cable conductor 385. As shown, the second opening 309 may be large enough so that the distal portion 302 of the interrupted cable conductor 385 may be cut or otherwise interrupted at each end of second opening 309 to yield and subsequently remove the segment 398 from the lead body 300. By cutting or interrupting the distal portion 302 of the interrupted cable conductor 385 at the second opening 309, electrical isolation between the proximal portion 388 of the selected cable conductor 385 and other cable conductors of the lead body 300 may be further enhanced.

The location of the second opening 309 along the distal portion 302 of the interrupted cable conductor 385 may be selected based on a desire to provide slightly more flexibility in the lead body 300 at the second opening 309. In one example, the second opening 309 may be a location at which a conductive element, such as an electrode or a shock coil, may be connected to a cable conductor of the lead body 300 other than the interrupted cable conductor 385.

In another example, a segment of the distal portion 302 of the interrupted cable conductor 385 between the first opening 308 and the second opening 309 may be removed by pulling or sliding that segment from the first opening 308 or the second opening 309. Similarly, the segment of the distal portion 302 of the interrupted cable conductor 385 between the second opening 309 and the distal end 302 of the lead body 300 may be removed by pulling or sliding that segment from the second opening 309 or the distal end 302 of the lead body 300.

In another embodiment, the entire distal portion 389 of the interrupted cable conductor 385 may be removed from the lead body 300. For example, assuming that friction between the distal portion 389 and the core jacket and/or outer jacket 305 of the lead body 300 is below some threshold, the distal portion 389 may be pulled from the lead body 300 at either the first opening 308 or the distal end 302 of the lead body 300, thus completely removing the distal portion 389 from the lead body 300. While this removal may further enhance electrical isolation between the proximal portion 388 of the interrupted cable conductor 385 and the other cable conductors of the lead body 300, flexibility along the portion of the lead cable 300 corresponding with the removed distal portion 389 of the interrupted cable conductor 385 may be increased. This flexibility may be advantageous in several cardiac therapy applications, such as, for example, CRT leads to be implanted in cardiac veins, as well as bradycardia and tachycardia therapy leads to be implanted into the right ventricle of the heart. In other applications, however, the original strength of the lead body 300 may be preferred over lead flexibility. In such applications, the interrupting of the distal portion 389 of the interrupted cable conductor 385, along with the possible removal of a relatively short segment of the distal portion 389, may be preferred over the complete removal of the distal portion 389.

After removal of either the segment 398 or the entirety of the distal portion 389 of the interrupted cable conductor 385, the electrical isolation of the cable conductors within the lead body 300 may be further improved by blocking potential fluid pathways between the cable conductors that may have been created by the removal of the segment 398 or the entirety of the distal portion 389. In one embodiment, at least a portion of a lumen that previously carried either the segment 398 or the entirety of the distal portion 389 of the interrupted cable conductor 385 may be filled with an electrically insulating material via the first opening 308, the second opening 309, and/or the distal end 302 of the lead body 300, depending on the extent of the lumen to be filled. In one example, the insulating material may acquire a liquid state when heated, thus allowing the insulating material to enter the lumen by suction, pressure, and/or other means. After cooling, the insulating material may then acquire a more solid state that retains substantial flexibility.

In another embodiment, the lead body 300 may be heated to reflow the outer jacket 305 and/or the core jacket, thus at least partially filling the portion of the lumen that previously carried either the segment 398 or the entirety of the distal portion 389 of the interrupted cable conductor 385. As additional material is not added to the lead body 300 in this embodiment, a high level of flexibility may be maintained in the portion of the lead body 300 corresponding to the removed segment 398 or entirety of the distal portion 389 of the interrupted cable conductor 385.

While the above discussion focuses on the interruption and related operations associated with a single selected cable conductor 385, similar operations may be performed on multiple cable conductors of the lead body 300. FIG. 9 is partial longitudinal side view of the example lead body 300 of FIG. 8, to which several conductive elements have been connected to the proximal portion of multiple interrupted cable conductors, resulting in a completed cardiac lead 900. In this example, each of the four cable conductors of the lead body 300 may be coupled to a separate conductive element 902, 904, 906, and 908. More specifically, conductive elements 902, 904, and 906 may be ring electrodes, with each ring electrode 902, 904, and 906 being positioned along the lead body 300 at a particular point between the proximal end 301 and the distal end 302 of the lead body 300 to be placed in contact with particular regions of the cardiac system of a patient. The conductive element 908 may be an end electrode 908 with an active-fixation structure (e.g., a corkscrew or helix structure) or a passive-fixation structure (e.g., one or more straight fins or tines) located at the distal end 302 of the lead body 300 to help physically anchor the lead body 300 to the cardiac system of the patient. Each of the electrodes 902, 904, 906, and 908 may be connected with its corresponding connector 392 by way of laser welding, resistance welding, swaging, crimping, bonding, or other means. In yet other examples, other types of conductive elements, such as shock coils, may be employed for the lead 900.

In this example, each of the three ring electrodes 902, 904, and 906 are mechanically and electrically connected to a distal end 395 of a proximal portion 388 of a corresponding cable conductor that has been cut or otherwise interrupted to form a proximal portion 388 and a distal portion 389. Further, the distal portion 395 of each of the three corresponding cable conductors has been removed from the lead body 300, and the lumens associated with the removed portions have been reflowed or filled with insulating material. In contrast, the cable conductor that is mechanically and electrically connected to the end electrode 908 at the distal end 302 of the lead body 300 is not interrupted, and thus extends from the proximal end 301 to the distal end 302 of the lead body 300.

Consequently, the resulting lead 900 exhibits four different sections 910, 912, 914, and 916 of differing flexibility based on the number of cable conductors remaining in that section. More specifically, the first section 910 between the proximal end 301 of the lead body 300 and the first ring electrode 902 includes four cable conductors, and thus exhibits the lowest relative flexibility of the four sections. The second section 912 between the first ring electrode 902 and the second ring electrode 904 includes three cable conductors, and is thus relatively more flexible than the first section 910 due to the removal from the lead body 300 of the distal portion 389 of the cable conductor connected to the first ring electrode 902. Similarly, the third section 914 between the second ring electrode 904 and the third ring electrode 906 includes two cable conductors, and is thus relatively more flexible than the second section 912 due to the removal from the lead body 300 of the distal portion 389 of the cable conductors connected to the first ring electrode 902 and the second ring electrode 904. Finally, the fourth section 916 between the third ring electrode 906 and the end electrode 908 includes a single cable conductor to connect the end electrode 908 to the proximal end 301 of the lead body 300, and is thus relatively more flexible than the third section 914 due to the removal from the lead body 300 of the distal portion 389 of the cable conductors connected to the ring electrodes 902, 904, and 906.

In other embodiments, the distal portion 389 of one or more of the cable conductors, after interruption, may be left as is, or may be interrupted again via one or more additional openings in the outer jacket 305 and/or core jacket, instead of being completely removed, to retain some higher level of rigidity within one or more of the sections 912, 914, and 916 of the resulting lead 900.

In the particular example of FIG. 9, as each electrode 902, 904, and 906 of the lead 900 is associated with a single cable conductor, the lead 900 may represent a unipolar lead, in which the return current path for each of the cable conductors in provided by the human body back to the source of the current (e.g., a pacemaker, defibrillator, or other cardiac therapy device) at the proximal end 301 of the lead body 300. In other examples, one or more additional cable conductors may be employed in the lead body 300 for the return current path for one or more of the electrodes 902, 904, 906, and 908, thus resulting in a bipolar lead. In yet other embodiments, more than one cable conductor may be coupled with a particular electrode 902, 904, 906, and 908, with one or more of those cable conductors being interrupted and subsequently processed, as described above.

Figure 10:
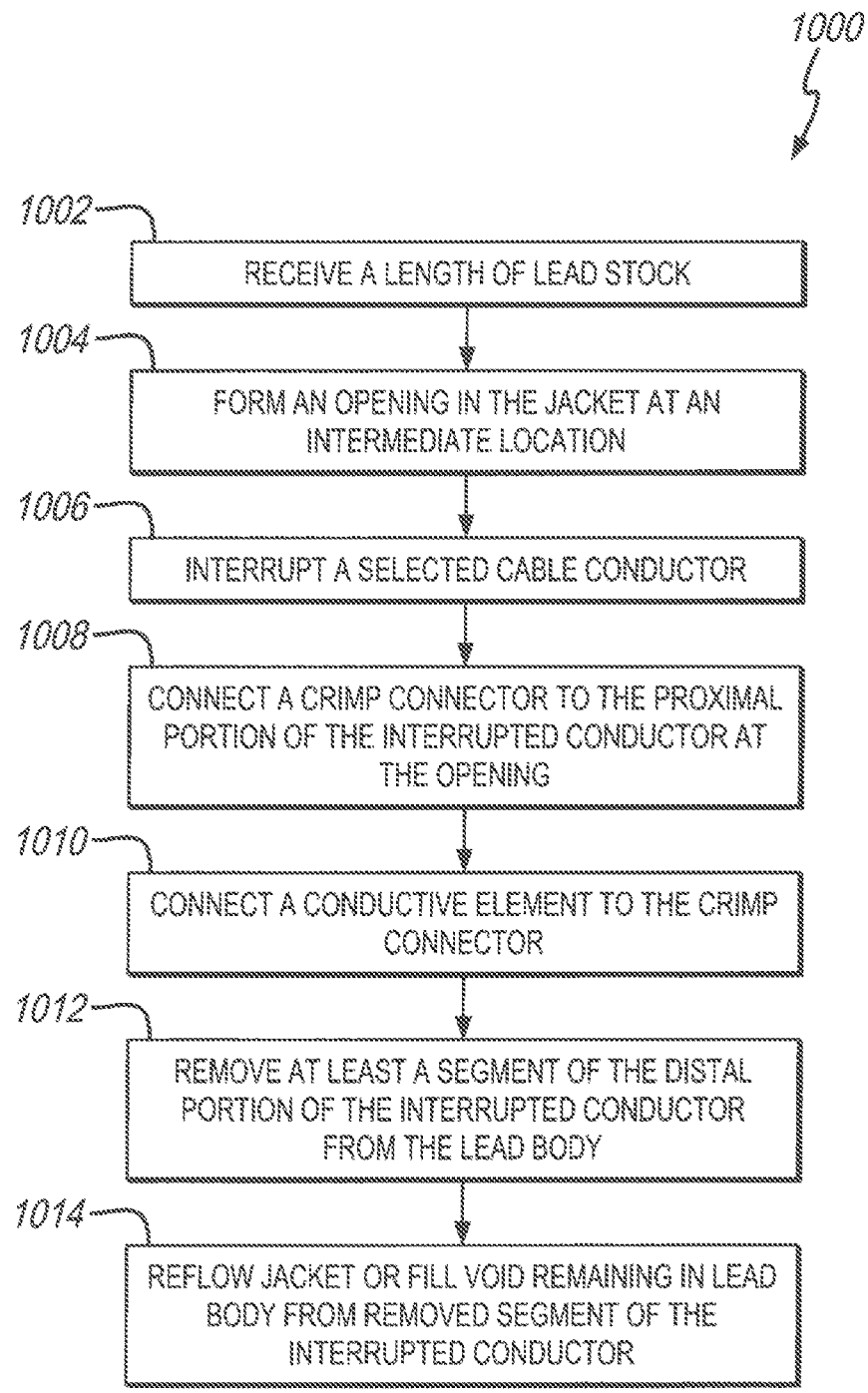
FIG. 10 is a flow diagram of an example method of manufacturing an implantable cardiac electrotherapy lead.

Based on the various embodiments of the lead body 300 described above, FIG. 10 is a flow diagram of an example method 1000 of manufacturing an implantable cardiac electrotherapy lead. In the method 1000, a length of lead stock may be received (operation 1002), such as from a spool or other container of stock. The lead stock may include multiple cable conductors, which may be helically wound, straight-routed, or otherwise arranged within the lead stock, as discussed above. The lead stock may also include an inner liner 120 with associated central lumen 140, a core jacket 125, and/or an outer jacket 105. The lead stock may be cut to a specific length corresponding to a particular cardiac therapy use, resulting in a lead body (e.g., lead body 300).

An opening 308 may then be formed in the core jacket and/or outer jacket 305 of the lead body 300 (operation 1004), such as by cutting or other means, and a selected cable conductor 385 of the lead body 300 may be interrupted (operation 1006) by way of cutting or other methods of separating the selected cable conductor 385 into a proximal portion 388 and a distal portion 389. Thereafter, a crimp connector 392 (e.g., the cylindrical crimp connector 600 of FIGS. 6A and 6B, or the crimp-through crimp connector 700 of FIGS. 7A-7D) or another type of connector may be connected to the proximal portion 388 of the interrupted cable conductor 385 at the opening 308 (operation 1008). A conductive element (e.g., one of the electrodes 902, 904, 906, or 908 of FIG. 9) may then be coupled to the connector (operation 1010), such as by welding, crimping, swaging, bonding, and the like.

To enhance electrical isolation of the proximal portion 388 of the interrupted cable conductor 385, at least a segment of the distal portion 389 of the interrupted cable 385, and possibly the entire distal portion 389, may be removed from the lead body 300 (operation 1012), such as by pulling or sliding the distal portion 389 from the first opening 308, a second opening 309, or the distal end 302 of the lead body 300. Thereafter, the core jacket and/or outer jacket 305 may be reflowed to fill a void in the lead body 300 created by the removal of a segment or entirety of the distal portion 389 of the interrupted cable conductor 385 (operation 1014). In another example, an insulating material may be employed to fill such a void (operation 1014). In some examples, operations 1004 through 1014 may be repeated for multiple cable conductors in the lead body 300, resulting in the lead 900 illustrated in FIG. 9.

While the operations 1002 through 1014 are shown as being performed in a particular order, other orders of performance for the operations 1002 through 1014 are also possible. For example, the connecting of the conductive element (operation 1010) may occur after the removal of the distal portion 389 of the interrupted cable conductor 385 (operation 1012) and the reflowing and/or filling operation (operation 1014). Other orders of performance of the operations 1002 through 1014 may also be possible.

Those skilled in the art will understand and appreciate that various modifications not explicitly described above may be made to the present disclosure and still remain within the scope of the present invention.

The resulting lead embodiments disclosed herein may be advantageous for several reasons. For example, the interrupting of a selected cable conductor may promote isolation of the selected cable conductors from other cable conductors in the lead. This isolation may be enhanced by the removal of a segment, or possibly the entirety, of the distal portion of the interrupted cable conductor. The possible reflowing of the core jacket and/or outer jacket of the lead, or the explicit filling of the lumens associated with the removed portion of the cable conductor using an insulating material, may further promote the electrical isolation between cable conductors. Additionally, the selective removal of segments or entire distal portions of interrupted cable conductors in the lead may facilitate enhanced flexibility in areas of the lead at which the cable conductors have been removed. Further, by selectively choosing particular areas of the lead for cable conductor removal, several different levels of flexibility along specific areas of the lead may be achieved.

Although the present invention has been described with reference to preferred embodiments, persons skilled in the art will recognize that changes may be made in form and detail without departing from the scope of the invention.

What is claimed is:

1. A method for manufacturing an implantable cardiac electrotherapy lead, the method comprising:
   receiving a length of lead stock, the length of lead stock comprising:
   a plurality of cable conductors; and
   an insulating jacket defining at least one lumen extending from a proximal end to a distal end of the length of the lead stock, the plurality of cable conductors located within the at least one lumen;
   forming an opening in the jacket at an intermediate location between the proximal end and the distal end of the length of lead stock;
   interrupting at least one of the cable conductors at the opening in the jacket to form a proximal portion and a distal portion of the at least one of the cable conductors;
   connecting a crimp connector to the proximal portion of the at least one of the cable conductors at the opening;
   connecting a conductive element to the crimp connector, wherein the conductive element is configured to administer an electrotherapy signal transmitted to the conductive element via the proximal portion of the at least one of the cable conductors; and
   removing at least a segment of the distal portion of the at least one of the cable conductors from the at least one lumen.

2. The method of claim 1, wherein the removing of the segment of the distal portion of the at least one of the cable conductors from the at least one lumen comprises removing an entirety of the distal portion of the at least one of the cable conductors from the at least one lumen.

3. The method of claim 2, wherein the removing of the entirety of the distal portion of the at least one of the cable conductors from the at least one lumen comprises sliding the distal portion of the at least one of the cable conductors from the at least one lumen from the distal end of the jacket.

4. The method of claim 1, wherein:
   the opening comprises a first opening in the jacket;
   the intermediate location comprises a first intermediate location between the proximal end and the distal end of the length of lead stock; and
   the removing of the segment of the distal portion of the at least one of the cable conductors from the at least one lumen comprises:
   forming a second opening in the jacket at a second intermediate location between the first intermediate location and the distal end of the length of lead stock;
   interrupting the at least one of the cable conductors at the second opening; and
   sliding a proximal segment of the distal portion of the at least one of the cable conductors from the at least one lumen via one of the first opening and the second opening.

5. The method of claim 1, wherein:
   the opening comprises a first opening in the jacket;
   the intermediate location comprises a first intermediate location between the proximal end and the distal end of the length of lead stock; and
   the removing of the segment of the distal portion of the at least one of the cable conductors from the at least one lumen comprises:
   forming a second opening in the jacket at a second intermediate location between the first intermediate location and the distal end of the length of lead stock;
   interrupting the at least one of the cable conductors at the second opening; and
   sliding a distal segment of the distal portion of the at least one of the cable conductors from the at least one lumen via one of the second opening and the distal end of the length of lead stock.

6. The method of claim 1, further comprising:
   filling, with insulating material, at least a portion of a void remaining in the at least one lumen resulting from the removing of the segment of the distal portion of the at least one of the cable conductors.

7. The method of claim 1, further comprising:
   reflowing the jacket to fill at least a portion of a void remaining in the at least one lumen resulting from the removing of the segment of the distal portion of the at least one of the cable conductors.

8. The method of claim 1, wherein:
   the opening in the jacket defines a proximal end and a distal end along the jacket; and
   the interrupting of the least one of the cable conductors comprises cutting the at least one of the cable conductors at the distal end of the opening.

9. The method of claim 1, the connecting of the crimp connector to the proximal portion of the at least one of the cable conductors at the opening comprising:
   stripping a portion of insulation covering the proximal portion of the at least one of the cable conductors;
   sliding the crimp connector over a distal end of the proximal portion of the at least one of the cable conductors, the crimp connector comprising a cylindrical crimp tube; and
   crimping the crimp connector onto the proximal portion of the at least one of the cable conductors.

10. The method of claim 1, the connecting of the crimp connector to the proximal portion of the at least one of the cable conductors at the opening comprising:
    sliding the crimp connector over a distal end of the proximal portion of the at least one of the cable conductors, the crimp connector comprising a crimp-through crimp tube; and
    crimping the crimp connector onto the proximal portion of the at least one of the cable conductors to cause the crimp connector to penetrate insulation covering the proximal portion of the at least one of the cable conductors to couple electrically the crimp connector with the proximal portion of the at least one of the cable conductors.

11. The method of claim 1, wherein the connecting of the conductive element to the crimp connector comprises one of:
    welding the conducting element to the crimp connector;
    swaging the conducting element to the crimp connector;
    crimping the conducting element to the crimp connector; and
    bonding the conducting element to the crimp connector.

12. A method of manufacturing an implantable cardiac electrotherapy lead, the method comprising:
    receiving a length of lead stock, the lead stock comprising:
    a plurality of cable conductors; and
    an insulating jacket defining, for each of the cable conductors, a lumen extending from a proximal end to a distal end of the length of the lead stock, each of the cable conductors extending along the jacket within its corresponding lumen, the cable conductors being helically wound about central axis oriented along the length of the lead stock;

cutting an opening in the jacket over a selected one of the cable conductors at an intermediate location between the proximal end and the distal end of the length of lead stock;

interrupting the selected cable conductor at the opening in the jacket to form a proximal portion and a distal portion of the selected cable conductor;

crimping a crimp connector to the proximal portion of the selected cable conductor at the opening;

connecting a conductive element to the crimp connector, wherein the conductive element is configured to administer an electrotherapy signal transmitted to the conductive element via the proximal portion of the selected cable conductor;

sliding an entirety of the distal portion of the selected cable conductor from the lumen corresponding to the selected cable conductor from the distal end of the length of lead stock; and performing one of:

filling, with insulating material, at least a portion of a void remaining in the lumen corresponding to the selected cable conductor; and reflowing the jacket to fill at least a portion of the void remaining in the lumen corresponding to the selected cable conductor.

\* \* \* \* \*